United States Patent
Razzano

(10) Patent No.: US 6,552,207 B2
(45) Date of Patent: Apr. 22, 2003

(54) PROCESS FOR THE PREPARATION OF AMPHOGLYCINATES FROM VEGETABLE OILS AND BUTTERS AND THE USE THEREOF

(75) Inventor: Gianni Razzano, Rozzano (IT)

(73) Assignees: VaMa Farmacosmetica S.r.l., Rozzano (IT); Fratelli Ricci-Fabbrica Prodotti Chimici S.r.l., Gorla Minore (IT)

( * ) Notice: Subject to any disclaimer, the term of this patent is extended or adjusted under 35 U.S.C. 154(b) by 31 days.

(21) Appl. No.: 09/794,650

(22) Filed: Feb. 27, 2001

(65) Prior Publication Data

US 2001/0018527 A1 Aug. 30, 2001

(30) Foreign Application Priority Data

Feb. 29, 2000 (IT) .................................. MI2000A000384

(51) Int. Cl.⁷ ............................................ C07C 231/00
(52) U.S. Cl. ....................................................... 554/68
(58) Field of Search ........................................... 584/68

(56) References Cited

PUBLICATIONS

Chem. Abstr., JP–05/246829, 1994.*

* cited by examiner

*Primary Examiner*—Deborah D. Carr
(74) *Attorney, Agent, or Firm*—Bucknam & Archer

(57) ABSTRACT

A process for the preparation of amphoglycinates from vegetable oils or butters, which comprises:
  a) reacting a source of vegetable triglycerids with aminoethylethanolamine in the presence of bases to give a hydroxyethylimidazoline of formula (II)

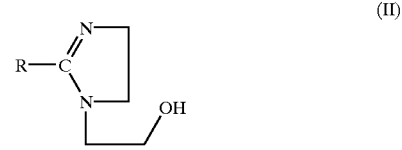

(II)

wherein R is the residue of the vegetable triglycerid fatty acid;
  b) reacting compound (II) with an alkali or alkaline-earth monohaloacetate at pH above 9, followed by acidification.

4 Claims, No Drawings

PROCESS FOR THE PREPARATION OF AMPHOGLYCINATES FROM VEGETABLE OILS AND BUTTERS AND THE USE THEREOF

The present invention relates to a process for the preparation of amphoglycinates from vegetable oils or butters.

Fatty acids amphocarboxylic derivatives have been known for a long time. The reaction for the preparation thereof has been studied by the Miranol Company in 1947, at first starting from coconut and tallow fatty acids: the obtained derivatives were used as tensides for household and industrial detergents. Subsequently they were studied for the use in cosmetic detergents, and when used as secondary tenside, they were found to exert equilibrating action on the skin irritation caused by primary tensides (American College of Toxicology, vol. 9,2, 1990).

The use in cosmetics obviously requires well-defined purity characteristics, which are hardly attained by the known preparation process, involving the use of fatty acids.

It has now been found a particularly convenient process, which can be applied to vegetable oils or butters and provides amphoglycinates particularly suitable for the cosmetic use.

More particularly, the direct use of vegetable triglycerids from, for example, pressing of seeds, provides an amphocarboxylate containing substances such as tocopherols, carotenoids, phytosterols and other unsaponifiables which can advantageously improve the functional characteristics of the amphocarboxylate itself as far as its formulation in cosmetic compositions is concerned.

Therefore, the invention relates to a process for the preparation of amphoglycinates of formula (I)

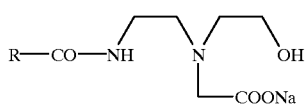
(I)

from vegetable oils or butters, which comprises:
  a) reacting a source of vegetable triglycerids with aminoethylethanolamine in the presence of bases to give a hydroxyethylimidazoline of formula (II)

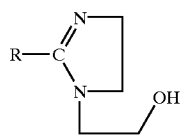
(II)

wherein R is the residue of the vegetable triglycerid fatty acid;
  b) reacting compound (II) with an alkali or alkaline-earth monohaloacetate at pH above 9, followed by acidification.

The invention further relates to the amphoglycinates obtainable by the process of the invention, the use thereof in the cosmetic field and cosmetic compositions containing them.

The vegetable triglycerid source is preferably selected from peanut, maize, sweet almonds, sesame, sunflower, avocado oils, cocoa butter, karité butter. The monohaloacetate is preferably sodium monochloroacetate.

Step a) is preferably carried out at temperatures ranging from 150 to 210° C., under reduced pressure.

Step b) is preferably carried out at pH above 10, more preferably at about pH 11, at a temperature of about 80° C.

During the acidification step, it is important to hydrolyze the monohaloacetate traces to sodium glycolate, in order to obtain a product compatible with the administration on the skin.

The amphocarboxylic derivatives obtainable according to the present invention are characterized in that they have high foaming power and are not sensitive to the hardness of water. Furthermore, they are compatible with the usual anionic, cationic and non-ionic tensides, can be mixed therewith and they reduce any skin irritant action thereof. Moreover, they are suitable in all the cosmetic formulations for cosmetic cleaning of the skin and have good compatibility with mucosae, hence being valuable as mild detergents. Finally, the derivatives of the invention do not have strong degreasing action on the skin or its adnexa (hair), thus exerting a detergent action without impoverishing the hydrolipidic films present on the skin and its adnexa. Therefore, the derivatives of the invention exert orthodermic detergent action and induce no "fly out" phenomena in the hair, which would require subsequent reconditioning treatments.

The following example illustrates the invention in greater detail.

EXAMPLE

The vegetable oil and aminoethyletanolamine (HEEA) are mixed in a reactor in a 2/1 ratio. The reaction chamber is subjected to high vacuum, then heated to a temperature of 180° C., slowly mixing for 2 hours. The mass is cooled to a temperature of 95° C., then diluted with 6 parts of hot water at a temperature of 90° C. The pH of the diluted mixture has to range from 11.5 to 12.

1 Part by weight of sodium monochloroacetate, calculated on 3 starting parts, is added. Mixing is continued for 2 hours keeping a temperature of 90° C. The progress of the reaction is checked by periodical titration of the non-ionic chlorine present in the mixture.

I claim:

1. A process for the preparation of amphoglycinates from vegetable oils or butters, which comprises:
  a) reacting a source of vegetable triglycerides with aminoethylethanolamine in the presence of bases to give a hydroxyethylimidazoline of formula (II)

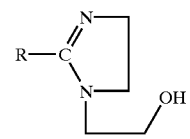
(II)

wherein R is the residue of the vegetable triglyceride fatty acid;
  b) reacting compound (II) with an alkali or alkaline-earth monohaloacetate at pH above 9, followed by acidification.

2. A process as claimed in claim 1, wherein the vegetable triglyceride source is selected from peanut, maize, sweet almonds, sesame, sunflower, avocado oils, cocoa butter, karité butter.

3. A process as claimed in claim 1, wherein step a) is carried out at a temperature ranging from 150° C. to 210° C.

4. A process as claimed in claim 1, wherein the monohaloacetate is sodium monochloroacetate.

* * * * *